United States Patent [19]

Jolicoeur et al.

[11] 4,043,987

[45] Aug. 23, 1977

[54] SUBSTITUTED AMMONIUM POLYPHOSPHATE COMPOSITION

[75] Inventors: Carmel Réjean Jolicoeur, Sherbrooke; Richard Riverin, Chomedey, both of Canada

[73] Assignee: Encoat Chemicals Limited, Montreal, Canada

[21] Appl. No.: 567,260

[22] Filed: Apr. 11, 1975

[30] Foreign Application Priority Data

Dec. 10, 1974 Canada .................................. 215811

[51] Int. Cl.² .................... C07D 251/66; C07F 9/02
[52] U.S. Cl. .............. 260/78.41; 260/2.5 R; 260/2.5 A; 260/29.6 MT; 260/29.6 MN; 260/29.6 MQ; 260/29.71; 260/29.7 N; 260/29.7 SQ; 260/45.7 P; 260/45.8 NT; 260/45.8 N; 260/45.8 NL; 260/501.21; 260/920; 260/926; 260/933; 428/411; 544/196
[58] Field of Search .................... 260/249.6, 920, 926, 260/933, 501.21, 78.41

[56] References Cited

U.S. PATENT DOCUMENTS

| 2,995,551 | 8/1961 | Reuter et al. ...................... 260/249.6 |
| 3,634,422 | 1/1972 | Nachbur et al. ................... 260/249.6 |
| 3,701,817 | 10/1972 | Maier ............................... 260/501.21 |
| 3,755,323 | 8/1973 | Weil et al. .......................... 260/249.6 |
| 3,887,553 | 6/1975 | Nachbur et al. ................... 260/249.6 |

FOREIGN PATENT DOCUMENTS 822,594  9/1969  Canada

*Primary Examiner*—Donald E. Czaja
*Assistant Examiner*—H. H. Fletcher
*Attorney, Agent, or Firm*—Bacon & Thomas

[57] ABSTRACT

Substantially water-insoluble, substituted ammonium polyphosphate compositions are provided, suitable as flame retardants in aqueous coating emulsions. The compositions are prepared by condensing together at an elevated temperature a condensed phosphoric acid and a spumific agent containing reactive nitrogen and optionally urea and/or a metal containing compound to form a solid foam, crushing the solid foam, to form a particulate material, and optionally curing the particulate material at an elevated temperature under pressure, without substantial weight loss.

21 Claims, No Drawings

SUBSTITUTED AMMONIUM POLYPHOSPHATE COMPOSITION

BACKGROUND OF THE INVENTION a. Field of the Invention

This invention relates to novel ammonium polyphosphates and their preparation; the invention is also concerned with compositions containing such polyphosphates as a flame retardant and to method of retarding flammability.

b. Description of Prior Art

Inorganic phosphorus-containing compounds are known as flame retarding compounds for a variety of substrates, and their use has been reported in various texts and patent disclosures, for example, Flame Retardancy of Polymeric Materials, Vol. 1, Edited by William C. Kuryla and A. J. Papa, 1973, published by Marcel Dekker, Inc., New York.

In particular the use of ammonium phosphates is well known. Such phosphate compounds may be blended in a coating formula or incorporated directly into a polymeric material, for example, polyurethane foam. While specific properties may be required for each particular application it seems generally acknowledged that for adequate flame retardancy the thermal decomposition curve of the flame retarding material must be similar to that of the substrate (W. G. Schmidt, Trans. J. Plastics Inst., December 1965, p. 247; J. A. Rhys, Chem. Ind. (London), 187 (1969)).

The development of various water based coatings has created a need for flame retarding compounds which are compatible with aqueous emulsions of polymers, for example, polyvinyl acetate emulsions. Generally, such compatibility requires that the flame retarding compound exhibit very low hygroscopy and low water solubility. The simple phosphates, for example, monoammoniumorthophosphate are generally water-soluble and hence unsuitable for aqueous emulsions. Furthermore, paint formulations containing water-soluble phosphates compare unfavourably with other paint formulations in washability, colour versatility and storage-ability; also the fire-retardant properties deteriorate with age due to the effect of weather and humidity on the water-soluble phosphate.

An ammonium polyphosphate of low water solubility is described in Canadian Pat. No. 822,594 — Paul G. Sears et al — issued Sept. 9, 1969; and this polyphosphate has found use in aqueous emulsions.

In addition to appropriate thermal decomposition and low water solubility other desirable properties or preparation features are desirable. For example, the product should be relatively easy to crush and grind into particles of such size as required for smooth application of coatings. Furthermore, the preparation should be as simple as possible, that is, controllable reactions involving mild conditions and a minimum amount of phases.

SUMMARY OF THE INVENTION

It is an object of the present invention to provide novel polyphosphate compositions which exhibit all of the above mentioned features to a degree equal or higher than the heretofore available materials. The compounds of the present invention are substantially water-insoluble and have been shown to be effective flame retardants when either coated on substrates or incorporated into rigid foam material.

It is a further object of the invention to provide a novel method for the production of the novel polyphosphate compositions.

It is a further object of the invention to provide paint or coating formulations containing a flame-retarding amount of the novel polyphosphate composition.

It is a further object of the invention to provide a porous foamed structural member of a polymeric, flammable material having a flame retarding amount of the novel polyphosphate composition.

It is a further object of the invention to provide a flammable substrate with a coating containing a fire retarding amount of the novel polyphosphate composition.

It is a still further object of the invention to provide a method of retarding flammability of a flammable substrate in which the substrate is treated with the novel polyphosphate composition.

The novel polyphosphates can be considered as compounds based on ammonium polyphosphate having a proportion of its ammonium radicals substituted by an organic nitrogenous spumific agent containing "reactive nitrogen".

The term reactive nitrogen refers to nitrogen in the form of amino, imino, or isocyanate; suitably the spumific agent will contain one or more groups selected from primary amine, secondary amine, tertiary amine, imino groups and isocyanate.

In this specification spumific agents, spumific substances or spumific compounds are to be understood as materials which, on heating, decompose to give gaseous products required for the formation of a froth or foam.

According to one aspect of the invention there is provided a substantially water-insoluble, substituted ammonium polyphosphate composition having the general formula (I)

$$Z_1-O[-(PO_3NH_4)_j-(PO_3R'N)_k-(PO_3)_mM)_{\frac{1}{m}}]_y Z_2 \quad (I)$$

wherein $Z_1$ and $Z_2$ are each selected from $-NH_4$ and $-R'N$, where N is a reactive nitrogen, $R'$ is the residue R or a fraction of the residue R of an organic nitrogenous spumific agent of general formula (II)

$$R(NH_2)_p(NH)_q(N)_r(NCO)_s \quad (II)$$

where $p$, $q$, $r$ and $s$ are integers from 0 to 6, and ($p + q + r + s$) is 1 or more; said spumific agent having a nitrogen to carbon ratio of 5 : 1 to 0.1 : 1, and a decomposition temperature above 150° C, and wherein $j$ is from 1 to 20, $k$ is 1 to 10, t is 0 to ($j + k$) and $y$ is 1 or more, and M is a polyvalent metal having a valency of $m$.

According to another aspect of the invention there is provided a process for preparing a substantially water-insoluble, substituted ammonium polyphosphate composition comprising i. a condensing together at an elevated temperature a condensed phosphoric acid and a spumific agent of general formula (II) as defined above to form a solid foam, ii. crushing the solid foam to form a particulate material, and optionally iii. curing the particulate material at an elevated temperature under pressure without substantial weight loss.

In one embodiment of the process urea is included in the condensation reaction in addition to the spumific agent and reacts with the condensed phosphoric acid.

According to another aspect of the invention there is provided an improved paint or coating formulation containing a film forming material and a solvent, the improvement comprising a fire-retarding amount of a substituted ammonium polyphosphate of general formula (I) as defined above.

In another aspect of the invention there is provided a coated flammable substrate, for example, a cellulose substrate, wherein the coating comprises a film forming material, and a fire retarding amount of a substituted ammonium polyphosphate of general formula (I) as defined above.

In another aspect of the invention there is provided a porous foamed structural member of a foamed polymeric flammable material having a flame retarding amount of a substituted ammonium polyphosphate of general formula (I) as defined above.

In another aspect of the invention there is provided a method of retarding flammability of a flammable substrate comprising treating the substrate with a composition containing a flame-retarding amount of a substituted ammonium polyphosphate of general formula (I) as defined above.

In particular and preferred embodiments in the spumific agent of formula (II), $p$ is an integer from 0 to 5, more preferably 1 to 3, $q$ is an integer of 0 to 4, more preferably 0 or 1, $r$ is 0 to 4, more preferably 0 to 3, $s$ is an integer of 0 to 4, more preferably 0 to 2, and $p + q + r + s$ is 2 to 8, more preferably 2 to 6; in a more specific embodiment the spumific agent contains only the elements selected from N, C, O and H; and has a high degree of unsaturation for a low C—H to C ratio.

Most organic amines or polyamines can be substituted into ammonium polyphosphates. However, not all are suitable for the present invention. The substituting amine must be a spumific agent with nitrogenous groups which can be converted to ammonium or immonium groups. The spumific agent should have a decomposition temperature above the temperature involved in the preparation of the polyphosphates of formula (I) to avoid appreciable thermal degradation, in this respect the decomposition temperature should be above 150° C and preferably not less than 200° C.

The spumific agent employed in the invention should have a nitrogen to carbon ratio of 5 : 1 to 0.1 : 1 and preferably a high degree of unsaturation; this ensures a low ratio of combustible to non-combustible gas formed during thermal degradation of the phosphates in use.

A further important requirement of the spumific agent is that it should form a substantially water-insoluble phosphate product.

In view of this it is preferred to avoid spumific agents of formula (II) wherein R contains functional groups, such as hydroxyl groups, which would render the polyphosphates of formula (I) more water-soluble. However, such solubilizing functional groups can be tolerated when urea is employed in the condensation reaction and the amount of spumific agent is small compared to the amount of urea.

Thus providing the water solubility of the polyphosphate is not significantly increased the radical R of the spumific agent may contain functional groups, for example, OH, —SH, C=O, CHO, COOH, NO, $NO_2$, NOH, —$SO_3H$, CN and $CONH_2$ as well as heteroatoms, for example, O, F. Cl, Br, P, S, B and Si.

Particularly preferred spumific agents are melamine, dicyandiamide, guanidine carbonate, tolylene diisocyanate, hexamethylene diisocyanate, polymers of these isocyanates and mixtures of any two or more thereof. Melamine is the particularly preferred spumific agent.

In the formula of the substituted ammonium polyphosphates, the degree of substitution by the spumific agent and the metal containing compound is specified by $k$ and $l$, and is varied by changing the ratio of spumific agent and metal containing compound to urea if present in the reaction. Production of the compound of formula (I) requires a ratio of phosphorus to reactive nitrogen of about 0.5 : 1 to about 2 : 1, part of the reactive nitrogens are supplied by the urea, if present, herein designated $N_u$, and part by the spumific agent, herein designated $N_s$. Theoretically the ratio of $N_s$ to $N_u$ can be varied infinitely, however, for practical embodiments the ratio $N_s : N_u$ varies from 1 : 0 preferably 1 : 0.1 to 1 : 20; similarly the ratio of metal to total reactive nitrogen groups may be varied from 0 to 50%. The designation y is a function of the degree of polymerization and depends on the temperature and duration of the final curing and can thus be any number of 1 or more.

Considering, by way of example, the use of melamine as the substituting spumific agent, one of the simplest forms of the melamine-ammonium phosphate has the general formula

where R is the aromatic nitrogen containing ring of melamine. In an actual preparation mixtures of branched and linear polymers are likely to occur.

A particular advantage of the substituted phosphates of the invention is that they are significantly easier to grind, for example, in a pebble mill, than heretofore available products. Further, their preparation is carried out under relatively mild experimental conditions. These reaction conditions are easily controllable and the time required for the condensation reaction may be as short as a few minutes. The reaction leading to the phosphate product of formula (I) of the invention is essentially a condensation reaction involving the reactive groups of the spumific agent of formula (II), a phosphorus oxy acid and optionally urea and/or a metal containing compound. The chemical inclusion of the spumific agent into the ammonium polyphosphate yields substituted polyphosphates of formula (I) exhibiting low hygroscopy and low water solubility, improved flame retardancy and good compatibility with aqueous emulsions.

The procedure for preparing the substituted polyphosphates of the present invention comprises a condensation reaction followed by an optional curing reaction. The condensation reaction involves mixing in an appropriate ratio the phosphorus oxy acid, the spumific agent of formula (II) and optionally urea and/or the metal containing compound. This mixture is then heated at a temperature and for a time required to form a solid foam; for the curing reaction the foam is crushed and heated under pressure for an extended period without subtantial weight loss.

In the condensation reaction any urea is suitably added to the phosphorus oxy acid with stirring to form a liquid mixture having a weight ratio of urea to acid of about 1 : 2 which gives a nitrogen to phosphorus ratio of about 1 : 1.5.

The spumific agent and optionally the metal containing compound are added in the form of fine powders to the liquid mixture and the reaction mixture is heated under condensation conditions to form a solid foam. During the condensation carbon dioxide and water are liberated with minor amounts of isocyanic acid and ammonia.

The condensation reaction is carried out at a temperature of 150° to 350° C for a period of a few minutes. Preferably the temperature is from 225° to 300° C and the reaction time is about 3 to 20 minutes.

Suitably the spumific agent is added to the liquid mixture in a molar ratio of spumific agent to phosphorus oxy acid of 0.03 : 1 to 1 : 1.

The phosphorus oxy acid employed in the invention is one having more than one P atom and having P—O—P bonds; such acids are polyphosphoric acids. A particularly suitable phosphoruc oxy acid is a condensed phosphoric acid containing one or more polyphosphoric acids and/or metaphosphoric acids and containing over 72% $P_2O_5$ by weight.

The optional curing reaction serves to render the polyphosphate product more water-insoluble, which is important for water-base paint formulations. When the polyphosphate product is employed in non-aqueous environments the curing step may be omitted. The polyphosphate product obtained from the condensation reaction itself generally has a water solubility of less than about 10% which is satisfactory for many applications.

In the curing reaction the solid foam condensation product is first crushed to coarse particles having a physical size corresponding to that of coarse sand or salt.

The crushed product is heated under pressure at a curing temperature without substantial weight loss. Suitably the curing temperature is from 150° to 300° C. The curing pressure is more than one atmosphere and preferably not greater than 30 atmospheres and more preferably less than 10 atmospheres. The curing time depends on the composition and the maximum tolerable solubility of the final product in water; suitably the curing time is from 0 to 48 hours and preferably 3 to 24 hours.

The cured product is composed of coarse particles having a coarseness similar to that of coarse sand; for use as a flame retardant the cured product is suitably crushed to a fine powder having an average particle size of about 25 microns. Examination under a microscope shows that these fine particles exhibit an irregular shape and cellular structure in marked contrast to prior phosphate products which have a distinctly glassy appearance.

It is also within the scope of this invention to include in the condensation reaction a fourth component comprising a carbonific agent having polyfunctional groups other than reactive amino groups, for example, polyols and polycarboxylic acids. In a few mole % such compounds do not adversely affect the flame retardant properties of the polyphosphate. In the case of polyols the hydroxyl groups may form ester units in the polyphosphate. Such fourth component may be, for example, ethylene glycol, glycerol, mono- and di-pentaerythritols and similar compounds.

As indicated above it is within the scope of this invention to include in the condensation reaction a minor amount of a metal containing compound for example, an oxide of a polyvalent metal. Suitable oxides include BaO, CaO, $TiO_2$, $SbO_2$, $Al_2O_3$, ZnO, $SiO_2$ and $B_2O_3$. Hydroxy compounds of these elements (hydroxides or acids) can also be employed in minor amounts.

These metal oxides or hydroxy compound additives may suitably be included in a molar ratio of additive to condensed phosphoric acid of 0 : 1 to 0.3 : 1. The metal oxides and hydroxide may react with the acid groups in the condensed phosphoric acid; the non-metal oxides, hydroxides and acids may react with the spumific agent.

As indicated previously the substituted polyphosphates of the invention are useful as fire retardant additives in solvent-based paint or coating formulations, particularly water-based formulations. Suitably such formulations comprise a dispersion of a binder or film-forming latex, intumescent solids and a pigment with a latex and intumescent solids comprising from about 30 to about 90% by weight of the total formulation.

The binder or film-forming latex is suitably of between about 30 to 80% solids by weight and is used in amounts to provide between about 10 and about 25% solids, by weight, of the total solids in the formulation. Suitable film-forming emulsions include vinyl acetate emulsions, copolymers of styrene and butadiene emulsions, acrylic emulsions, vinyl chloride emulsions, vinylidene chloride emulsions and copolymers and terpolymers of these polymer materials.

The intumescent solids comprise spumific compounds and carbonific or carbon-yielding substances. Suitably the intumescent solids form about 65 to 90%, by weight, of the total solids in the composition; the spumifics forming about 10 to about 75% by weight of the intumescent solids; and the carbonific solids forming about 10 to 35% of the total weight of intumescent solids to a total of 100%.

The polyphosphates of formula (I) are suitable spumific compounds for the intumescent solids and they may comprise all or a major part of the spumific compounds in the intumescent solids. It is preferred, however, to employ as the spumific compounds a major portion of the polyphosphates of formula (I) and a lesser portion of a conventional spumific agent, for example, melamine, dicyandiamide and mixtures thereof.

The carbonific substances may be selected from resinous and non-resinous carbonifics and include urea-formaldehyde resin; melamine-formaldehyde resin; modified starches; polyhydric compounds, for example, hexitols, pentitols, mono-tetritols and di-tetritols and solid chlorinated paraffins.

Various other additives may be incorporated into the formulations, in addition to the pigments or dye there may be included swelling agents, wetting agents, dispersing agents, fungicides, and the like; such additives are employed in minor amounts generally less than 15% by weight of the total weight of the formulation.

The formulation may further include a plasticizer for the latex, if necessary.

A typical formulation has a solids content of 15% polymer resin; 15% of a polydric compound and 9% of a chlorinated paraffin as carbonific substances; with 46% of a polyphosphate of formula (I) and 15% of a spumific agent, for example, dicyandiamide as spumific compound.

In preparing the water-base formulations, water and the ingredients are mixed and ground together in a pebble mill, usually for about 4 to 24 hours.

EXAMPLES

The invention is illustrated in preferred embodiments by reference to the following Examples.

EXAMPLE 1

47 g. of urea were added, while mixing, to 100 g. of condensed phosphoric acid; 8 g. of melamine were then added to the resulting liquid mixture and the whole was placed in an oven at 240° C. for 10 minutes. Following this heat treatment 134 g. of a foamed solid was recovered. When a 10% weight aqueous slurry of the foamed solid was agitated for 30 minutes at 25° C., the water solubility of the solid was measured as 5.4 g. per 100 cm$^3$ of water; the pH of the slurry was 5.68.

The remaining foamy condensate solid was crushed and heat cured in a pressurized metal vessel at a pressure of 4 atmospheres; the heat curing was carried out at 170° C for 13 hours. The solubility of the cured product, again measured from a 10% weight slurry, was 3.92 g./100 cm$^3$ of water at 25° C and the pH of this slurry was 6.63. The curing heat treatment involved no substantial weight loss of the foamed solid produced in the condensation.

On analysis the product was found to have the following composition:

C, 4%; N, 18%; P, 29%; H, 4%; O, 45%.

The X-ray diffraction pattern for the substituted ammonium polyphosphate product is as follows:

| Line | 2θ | d,A |
|---|---|---|
| 1 | 14.71 | 6.017 |
| 2 | 15.52 | 5.705 |
| 3 | 15.91 | 5.564 |
| 4 | 16.34 | 5.420 |
| 5 | 23.34 | 3.808 |
| 6 | 24.87 | 3.577 |
| 7 | 25.49 | 3.491 |
| 8 | 26.09 | 3.412 |
| 9 | 27.59 | 3.230 |
| 10 | 28.34 | 3.146 |
| 11 | 28.84 | 3.093 |
| 12 | 29.74 | 3.002 |
| 13 | 30.54 | 2.925 |
| 14 | 30.99 | 2.883 |
| 15 | 31.74 | 2.817 |
| 16 | 32.57 | 2.747 |
| 17 | 33.96 | 2.638 |
| 18 | 35.34 | 2.538 |
| 19 | 37.19 | 2.416 |
| 20 | 38.24 | 2.352 |
| 21 | 39.34 | 2.288 |

The thermal decomposition of the polyphosphate of Example 1 was measured as a function of time and compared with that of Phoscheck P-30 (trademark) an ammonium polyphosphate available from Monsanto Company, believed to be made according to the aforementioned Canadian Pat. No. 822,594; the two samples were of similar particle size.

| Temperature 250° C sample weight | Invention 0.3233 gr | Phoscheck P-30 (trademark) 0.4485 gr |
|---|---|---|
| % wt loss after 1 hour | 2.83 | 1.92 |
| % wt loss in 2nd hr | 0.47 | 0.49 |
| % wt loss after 2 hrs | 3.30 | 2.41 |
| Temperature 275° C sample weight | 0.3555 gr | 0.4004 gr |
| % wt loss after 1 hour | 2.91 | 1.47 |
| % wt loss in 2nd hr | 0.63 | 0.65 |
| % wt loss after 2 hrs | 3.54 | 2.12 |
| % wt loss in 3rd hr | 0.58 | 0.71 |
| % wt loss after 3 hrs | 4.29 | 2.83 |

From these results it can be seen that the invention product of Example I loses gaseous products by thermal decomposition at a greater rate than Phoscheck P-30 (trademark), and thus the product of Example 1 provides a superior flame retardant.

EXAMPLE 2

To a liquid mixture containing, as in Example 1, 46 g. of urea and 100 g. of condensed phosphoric acid was added 12 g of dicyandiamide. The mixture was heated in an oven at 240° C for 10 minutes, and 132 g. of a solid foamy material was recovered, which was highly soluble in water. The solid was heat cured in the manner described in Example 1. The curing reaction yielded a product for which the water solubility (10% weight slurry stirred for 30 min. at 25° C) was 8.23 g./100 cm$^3$ of water; the pH of the 10% weight slurry was 7.11.

The following Examples were carried out using the procedure described in Example 1, the conditions were the same as in Example 1, except where otherwise stated.

Example 3:

| | |
|---|---|
| Condensed phosphoric acid: | 100 gr. |
| + Urea: | 45 gr. |
| + Guanidine carbonate: | 10 gr. |

(formula of Guanidine carbonate: $H_2N-\underset{\underset{NH}{\|}}{C}-NH_2 \cdot H_2CO_3$)

Condensing at 200° C for 15 minutes
Curing at 170° C for 12 hours
Properties: pH of 10% wt slurry 7.45
Solubility of 10% wt slurry 7.06 gr./100 ml.

Example 4:

| | |
|---|---|
| Condensed phosphoric acid: | 100 gr. |
| Urea: | 45 gr. |
| Melamine: | 8 gr. |
| Pentaerythritol: | 4 gr. |

Condensing at 240° C for 15 minutes
Curing at 170° C for 12 hours
Properties: pH of 10% wt slurry 5.47
Solubility of 10% wt slurry 6.4 gr./100 ml.

Example 5:

| | |
|---|---|
| Condensed phosphoric acid: | 100 gr. |
| Urea: | 40 gr. |
| Melamine: | 10 gr. |
| Inositol: | 5 gr. |

Condensing at 225° C for 12 minutes
Curing at 170° C for 12 hours
Properties: pH of 10% wt slurry 6.50
Solubility of 10% wt slurry 5.8 gr./100 ml.

Example 6:

| | |
|---|---|
| Condensed phosphoric acid: | 100 gr. |
| Urea: | 45 gr. |
| Melamine: | 5 gr. |
| Ethylene glycol: | 10 gr. |

Condensing at 200° C for 15 minutes
Curing at 170° C for 18 hours
Properties: pH of 10% wt slurry 6.15
Solubility of 10% wt slurry 6.6 gr./100 ml.

Example 7:

| | |
|---|---|
| Condensed phosphoric acid: | 100 gr. |
| Urea: | 45 gr. |
| Melamine: | 6 gr. |
| Aluminium oxide: | 5 gr. |

Condensing at 250° C for 10 minutes
Curing at 170° C for 16 hours
Properties: pH of 10% wt slurry 6.62
Solubility of 10% wt slurry 4.7 gr./100 ml.

Example 8:

| | |
|---|---|
| Condensed phosphoric acid: | 100 gr. |
| Urea: | 45 gr. |
| Melamine: | 6 gr. |
| Silicic acid: | 4 gr. |
| Condensing at 240° C for 10 minutes | |
| Curing at 170° C for 12 hours | |
| Properties: pH of 10% wt slurry 6.06 | |
| Solubility of 10% wt slurry 5.9 gr./l. | |

An important aspect of the present invention is that the spumific agent is incorporated into the polyphosphate without significant degradation. This is readily seen by comparison of the ultra-violet absorption spectra of melamine and the substituted ammonium polyphosphate described in Example 1. It was also found that there remained no significant portion of undecomposed urea.

As illustrated in the above Examples, the substituted ammonium polyphosphates of the invention are only moderately soluble in water. It is especially noteworthy that in some cases, e.g., with melamine in Example 1, the polyphosphates obtained are much less soluble in water than the ammonium polyphosphates in the aforementioned Canadian Pat. No. 822,594 and prepared under the process conditions of Example 1 of the present invention.

The thermal decomposition of the polyphophates of the invention has been shown to occur substantially faster than that of the ammonium polyphosphate heretofore available. This is well illustrated by comparison of TGA Curves for the commercial ammonium polyphosphate of Canadian Pat. No. 822,594 and the substituted polyphosphates of Example 1 above. This feature of the substituted polyphosphates gives an improved match between the thermal decomposition of substrates, for example, cellulose or polymeric foam and the thermal decomposition of the substituted ammonium polyphosphates. This is believed to be responsible for the excellent intumescence obtained when the compounds of the invention are added in coating formulations for cellulosic substrates, or incorporated directly into rigid polymeric foam, for example, polyurethane.

Finally, compared to the ammonium polyphosphates of Canadian Pat. No. 822,594, the substituted ammonium polyphosphates of the invention are substantially easier to grind and consequently their formulation into coating compositions is facilitated.

We claim:

1. A substantially water-insoluble substituted ammonium polyphosphate composition having the general formula (I)

$$Z_1-O[-(PO_3NH_4)_j-(PO_3R'N)_k-]_yZ_2 \qquad (I)$$

wherein $Z_1$ and $Z_2$ are each selected from —$NH_4$ and —NR', N is a reactive nitrogen, R' is the residue R, of an organic nitrogenous spumific agent of general formula (II)

$$R(NH_2)_p(NH)_q(N)_r \qquad (II)$$

wherein $p$, $q$ and $r$ are integers from 0 to 6 and $(p + q + r)$ is 1 or more; said spumific agent hving a nitrogen to carbon ratio of 5 : 1 to 0.1 : 1, and a thermal decomposition temperature above 150° C, and wherein $j$ is from 1 to 20, $k$ is 1 to 10 and $y$ is 1 or more.

2. A composition according to claim 1, wherein p is an integer from 0 to 5, $q$ and $r$ are each integers of 0 to 4 and $p + q + r$ is 2 to 6.

3. A composition according to claim 1, wherein R contains at least one functional group selected from —OH, —SH, CO, CHO, COOH, NO. $NO_2$, NOH, —$SO_3H$, CN, $CONH_2$.

4. A composition according to claim 1, wherein R contains at least one heteroatom selected from O, F, Cl, Br, P, S, B and Si.

5. A composition according to claim 2, wherein said spumific agent contains only elements selected from the group consisting of N, C, O and H.

6. A composition according to claim 1 wherein said spumific agent is selected from melamine, dicyandiamide, guanidine carbonate and mixtures thereof.

7. A substantially water-insoluble, substituted ammonium polyphosphate composition having the general formula (I)

$$Z_1-O[-(PO_3NH_4)_j-(PO_3R'N)_k-]_yZ_2 \qquad (I)$$

wherein $Z_1$ and $Z_2$ are each selected from —$NH_4$ and —NR', N is a reactive nitrogen, R' is the residue R of an organic nitrogenous spumific agent of general formula (II)

$$R(NH_2)_p(NH)_q(N)_r \qquad (II)$$

wherein $p$ is an integer of 1 to 3, $q$ is 0 or 1, $r$ is an integer of 0 to 3 and $(p + q + r)$ is 2 to 6; said spumific agent having a nitrogen to carbon ratio of 5 : 1 to 0.1 : 1, and a thermal decomposition temperature above 150° C, said spumific agent having a high degree of unsaturation and being thermally decomposable to gaseous products containing non-combustible gas, and wherein $j$ is from 1 to 20, $k$ is 1 to 10, and $y$ is 1 or more.

8. A composition according to claim 7 wherein said spumific agent is melamine.

9. A process for preparing a substantially water-insoluble substituted ammonium polyphosphate composition comprising
   i. condensing together at an elevated temperature a condensed phosphoric acid containing more than 72% $P_2O_5$, by weight, and containing one or more phosphoric acids selected from the group consisting of polyphosphoric acids and metaphosphoric acids, and a spumific agent of general formula (II)

$$R(NH_2)_p(NH)_q(N)_r \qquad (II)$$

wherein $p$, $q$ and $r$ are integers from 0 to 6 and $(p + q + r)$ is 1 or more, and said spumific agent has a nitrogen to carbon ratio of 5 : 1 to 0.1 : 1, and a decomposition temperature above 150° C, to form a solid foam, and
   ii. crushing the solid foam to form a particulate material.

10. A process according to claim 9, including the further step of curing the particulate material at an elevated temperature under pressure, without substantial weight loss.

11. A process according to claim 9, wherein urea is included in said condensing step.

12. A process according to claim 9, wherein $p$ is an integer from 0 to 5, $q$ and $r$ are integers of 0 to 4, and $p + q + r$ is 2 to 6.

13. A process according to claim 10, wherein said condensing is carried out at a temperature of 150° to 350° C and said curing is carried out at a temperature of 150° to 300° C for 3 to 24 hours at a pressure more than 1 and less than 30 atmospheres.

14. A process according to claim 9, wherein said condensing is carried out at a temperature of 225 to 300° C for 3 to 20 minutes.

15. A process according to claim 10, including the step of grinding the cured product to a fine powder having an average particle size of about 25 microns.

16. A process according to claim 9, wherein in said condensing there is included a few mole % of a polyhydric compound.

17. A process according to claim 9, wherein said condensing is carried out in a liquid state.

18. A process according to claim 9, wherein in said condensing there is included a compound of a polyvalent metal.

19. A process according to claim 9, wherein said spumific agent is selected from melamine, dicyandiamide, guanidine carbonate and mixtures thereof.

20. A process according to claim 9, wherein $p$ is an integer of 1 to 3, $q$ is 0 or 1 and $r$ is an integer from 0 to 3 and $(p + q + r)$ is 2 to 6; said spumific agent of formula (II), having a high degree of unsaturation and being thermally decomposable to gaseous products containing non-combustible gas.

21. A process according to claim 20 wherein said spumific agent of formula (II) is melamine.

* * * * *